United States Patent [19]

Theodoridis et al.

[11] Patent Number: 4,980,480
[45] Date of Patent: Dec. 25, 1990

[54] PRODUCTION OF TRIAZOLINONES

[75] Inventors: George Theodoridis, Princeton; John W. Lyga, Basking Ridge, both of N.J.

[73] Assignee: FMC Corporation, Philadelphia, Pa.

[21] Appl. No.: 405,179

[22] Filed: Sep. 8, 1989

[51] Int. Cl.$^5$ .......................................... C07D 249/12
[52] U.S. Cl. .............................. 548/263.2; 548/263.8
[58] Field of Search ........................... 548/263.2, 263.8

[56] References Cited

U.S. PATENT DOCUMENTS 4,818,275  4/1989  Theodoridis ............................ 71/92

FOREIGN PATENT DOCUMENTS 63-93768   4/1989  Japan .
87-03782   7/1987  PCT Int'l Appl. .
2021586   12/1979 United Kingdom .

OTHER PUBLICATIONS

Derwent Abstracts, Accession No. 85-213,758/35, abstract of J60-136,572 (Japan) published 7/20/85.

*Primary Examiner*—Glennon H. Hollrah
*Assistant Examiner*—Patricia L. Morris
*Attorney, Agent, or Firm*—Robert M. Kennedy; H. Robinson Ertelt; Abner Sheffer

[57] ABSTRACT

Process for the production of an aryl triazolinone of the formula:

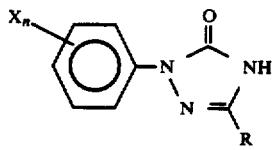

Formula I in which
R is halogen, alkyl, haloalkyl, cyanoalkyl, arylalkyl, alkoxyalkyl, alkylthio, alkylsulfinyl, alkylsulfonyl, alkylthioalkyl, alkylsulfinylalkyl, alkylsulfonylalkyl or phenyl,
each X is independently, H, halogen, lower alkyl, lower alkoxy, $-NO_2$, $-OH$, $-NHSO_2R'$, $-N(SO_2R')_2$ or $-N(R')SO_2R'$ where R' is lower alkyl, and n is a number from 1 to 3,
by treating an aryl triazolidinone of the formula:

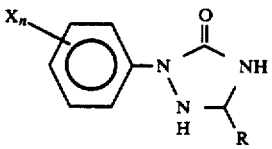

Formula II with a halogen of the group consisting of chlorine, bromine and iodine, or a hypohalous acid of said halogen or a salt of said acid.

13 Claims, 7 Drawing Sheets

FIGURE 7
OTHER ANILINE STARTING MATERIALS

PRODUCTION OF TRIAZOLINONES

The invention relates to the production of aryl 1,2,4-triazolin-5-ones.

Japanese published application No. 60-136572 published July 20, 1985 (hereafter the "J85 application") discloses the production of an aryl triazolinone of the formula:

Formula I (in which R may be a lower alkyl or phenyl, each X may be, independently, H, halogen, lower alkyl, lower alkoxy, nitro or OH, and n is a number from 1 to 3) from an aryl triazolidinone of the formula:

Formula II

The reaction is effected by heating the compound of Formula II in the presence of a base and a solvent; an interphase transfer catalyst such as tetra-n-butylammonium bromide may be present.

Japanese published application No. 63-093768 published Apr. 25, 1988 (hereafter the "J88 application") discloses a process for producing compounds of Formula I by oxidizing a compound of Formula II with air, oxygen, hydrogen peroxide or certain organic peroxygen compounds.

In the process described in the J85 application (as in an earlier U.K. patent No. 2,021,586) the aryl triazolidinone may be produced by reacting an aryl hydrazine with acetaldehyde to form a hydrazone and then treating with sodium cyanate. The reaction of the hydrazone with an alkaline cyanate to form the compound of Formula II is disclosed in the earlier U.K. patent No. 2,021,586.

In accordance with one aspect of the present invention, a triazolidinone (such as a compound of Formula II) is treated with hypochlorite (such as sodium hypochlorite, aqueous hypochlorous acid or another salt of hypochlorous acid, such as an alkali metal or alkaline earth metal salt, e.g. calcium or lithium hypochlorite) or with chlorine, to form a triazolinone (such as a compound of Formula I). It is found that the reaction proceeds rapidly at relatively low temperatures to give high yields in short reaction times. For instance, as illustrated in Example I below, a yield of greater than 80% was obtained at room temperature practically instantaneously, starting with the very same 3-nitrophenyl-3-methyl-1,2,4-triazolidin-5-one as is employed in the single Example of the J85 application. In contrast, the J85 Example discloses heating for 4 hours at 80° C. to produce a yield of 62%.

The aryl triazolidinones (such as the compounds of Formula II) are usually produced from the corresponding aryl amines, via their hydrazines. In the J85 application the compound of Formula II is produced (by forming the hydrazone from the hydrazine and reacting the hydrazone with a cyanate) and then isolated prior to reaction with the base. For the reactions of the present invention, (e.g. the reaction with sodium hypochlorite) it is not necessary to separate the aryl triazolidinone from the crude reaction mixture obtained in the reaction used to form that compound. Thus, one may add the hypochlorite or chlorine to the triazolidinone-containing reaction mixture obtained by treating an aryl hydrazone with the cyanate. The latter reaction mixture may, in turn, be obtained by reacting an aryl hydrazine with acetaldehyde and then, without isolating the resulting hydrazone, reacting with the cyanate.

The exact mechanism of the reaction of the present process is not known at this time. It is possible that it may involve the chlorination of a ring nitrogen of the triazolidinone to form an N-chloro compound, followed by decomposition of the latter with the elimination of HCl.

The reaction is preferably carried out in a medium in which the triazolidinone is at least partially soluble. One very suitable medium is acetic acid which may be anhydrous or may contain water. As indicated above, reaction at room temperature has given very good results; temperatures higher or lower than that may be used if desired (e.g. temperatures in the range of about 0° to 100° C., preferably about 10° to 50° C.). In the Examples below the reaction was carried out at atmospheric pressure; however, subatmospheric or super-atmospheric pressure may be employed. Proportions to provide about one atom, or more, of Cl per molecule of triazolidinone are preferred. With larger amounts (and longer reaction times) one may also effect ring-chlorination of the aromatic ring of the aryl triazolinone, which is often desirable; see, for instance Example 9, below, as well as Example 7.

The amount of reaction medium may be so chosen that the desired triazolinone precipitates, or otherwise separates, from the reaction mixture, as illustrated in the Examples below. The reaction may be carried out at an acidic pH (as in Example 1 in which the pH is substantially that of acetic acid, i.e. about pH 4 to 5) or at an alkaline pH, as in Example 3 in which the pH is substantially that of the sodium hypochlorite, i.e. about pH 11.

As indicated above, the reaction of this invention may be carried out on a reaction mixture obtained from previous steps of hydrazone formation (e.g. with acetaldehyde) and triazolidinone formation (e.g. with an alkaline cyanate). Such reaction mixtures may contain, for instance, byproducts, or unreacted reactants, of the previous reactions.

While it is preferred to employ chlorine or hypochlorite in the process of this invention, it is within the broader scope of the invention to substitute bromine or a hypobromite or iodine or a hypoiodite, for all, or part of the chlorine or hypochlorite.

As shown in Examples 8 and 9 the invention is also useful for compounds in which X (in Formulas I and II) is $-NHSO_2R'$ where $R'$ is lower alkyl. Other X substituents are $-N(SO_2R')_2$ and $-N(R')SO_2R'$. The R substituent may also be one of those designated as $R^3$ in column 1 lines 48 to 59 of U.S. Pat. No. 4,818,275; thus R may be halogen (e.g. chlorine), alkyl (e.g. of 1 to 5 carbon atoms), haloalkyl (e.g. of 1 to 5 carbon atoms such as difluoromethyl), alkoxyalkyl (e.g. of 2 to 6 carbon atoms such as methoxymethyl), cyanoalkyl (e.g. of 2 to 6 carbon atoms such as cyanomethyl), arylalkyl such as benzyl, alkylthio (e.g. of 1 to 3 carbon atoms such as methylthio) or the corresponding alkylsulfinyl or alkylsulfonyl, or alkylthioalkyl (e.g., of 1 to 3 carbon atoms independently with respect to each alkyl, such as methylthiomethyl) or the corresponding alkylsulfinylalkyl or alkylsulfonylalkyl.

The invention is useful, for example, in the production of herbicides such as those shown in U.S. Pat. No. 4,818,275, whose entire disclosure is incorporated herein by reference, such as compound no. 1 of Table 1 of that patent. The accompanying drawings illustrate various starting materials, reaction sequences and intermediates involved in processes for making that compound no. 1. More particularly:

In the illustrated reaction sequences the individual steps may be carried out in known manner. For instance, the conversion of the aromatic amines (such as compounds 5, 19, 30, 38, 57–60) to their hydrazones (compounds 6, 12, 21, 35, 32, 46 and 40) is conventionally carried out by forming the hydrazine (as by diazotization and reduction) and then reacting with acetaldehyde (or with acetone for compound 46). The hydrazones may be reacted with an alkali metal cyanate, such as NaOCN or KOCN, to form the aryltriazolidinones (such as compounds 7, 13, 22, 36, 33, 47 and 41) which may in turn be oxidized to form the aryltriazolinones (such as compounds 8, 14, 23, 25, 24 and 42) by the method of this invention. (Compound 47 may be converted to the triazolinone by reaction with acetyl chloride or acetic anhydride to form compound 48, followed by heating in the presence of acid to form compound 24). The introduction of the difluoromethyl group may be effected by reaction with $CClF_2H$ in the presence of a base. Nitrations (e.g. to convert compound 1 to compound 2, or 25 to 26, or 37 to 27, or 14 to 42, or 15 to 43) may be carried out with nitric acid in concentrated or fuming sulfuric acid, and conversions of the nitro groups to amino groups may be effected under conventional reducing conditions. The introduction of the alkylsulfonyl group onto the amino group may be effected in the ways described in U.S. Pat. No. 4,818,275. Chlorination of the phenyl ring (as in the following conversions: 6 to 49, 9–10, 14–23, 14–25, 15-16, 15–37, 16–37, 9–10, 45–10) may be carried out with such agents as chlorine or sulfuryl chloride or with sodium hypochlorite (as indicated in Example 9); in some cases it may be desirable to first employ sulfuryl chloride to place a chlorine atom at the 4-position (as in converting compound 14 to compound 23) and then to employ chlorine, in the presence of a catalyst such as iron, to place a second chlorine atom at the 2-position (as in converting compound 23 to compound 25).

As indicated in Examples 5 and 8, the hydrazone may be produced, in a single pot, from the aniline, without separating the intermediate hydrazine; in those Examples the reduction of the diazo compound is effected with stannous chloride, but it will be understood that other agents conventionally employed for such reduction (such as sodium bisulfite) may be used instead.

It should be understood that the reaction sequences illustrated in the drawing may be varied and that an intermediate produced in one illustrated sequence may be further reacted according to a series of reactions which forms part of another illustrated sequence.

The following Examples are given to illustrate this invention further. In these Examples all proportions are by weight, all temperatures are in degrees C. and pressures are atmospheric, unless otherwise indicated.

EXAMPLE 1

Figure 5:
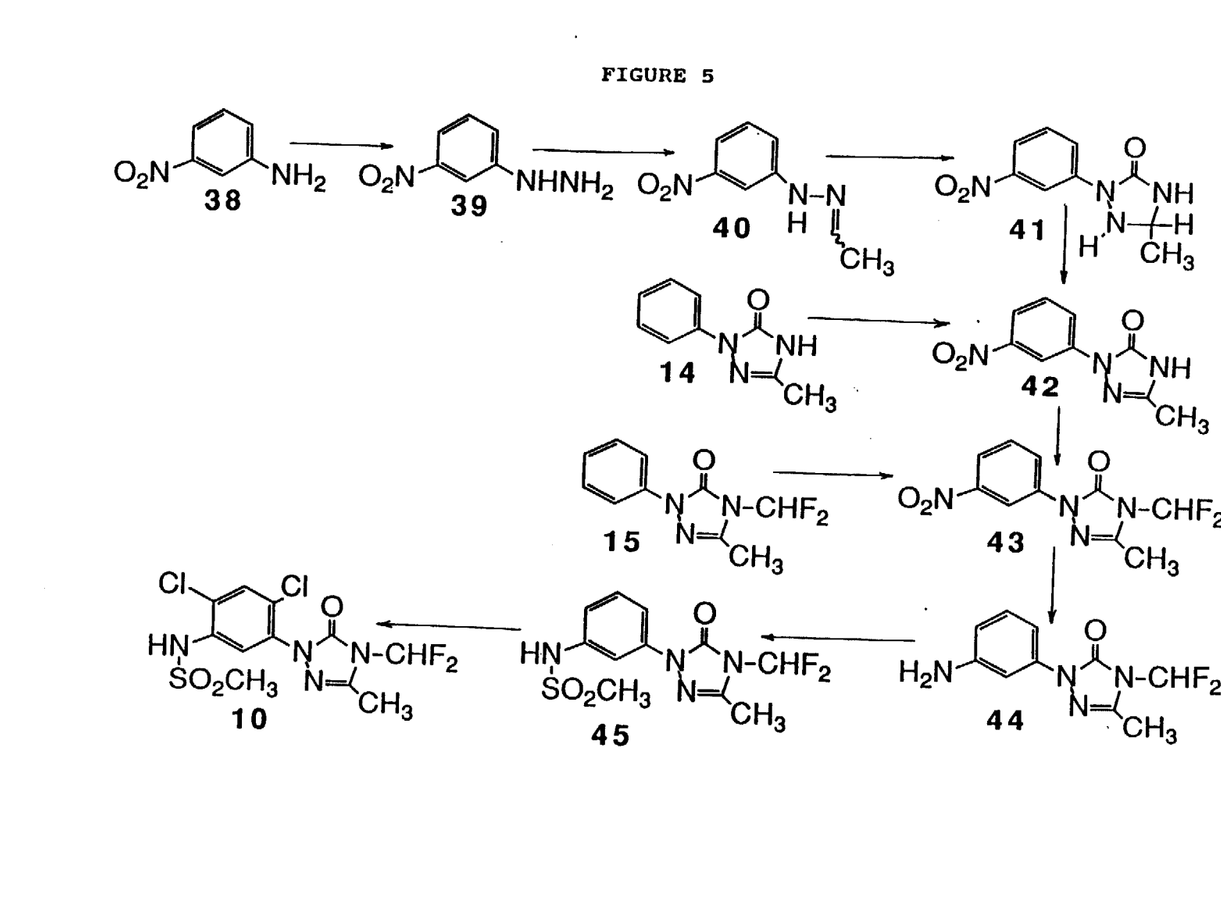
FIG. 5 shows reaction sequences starting with 3-nitroaniline, or with intermediate 14 of FIG. 2, or with intermediate 15 of FIG. 2.
Figure 6:
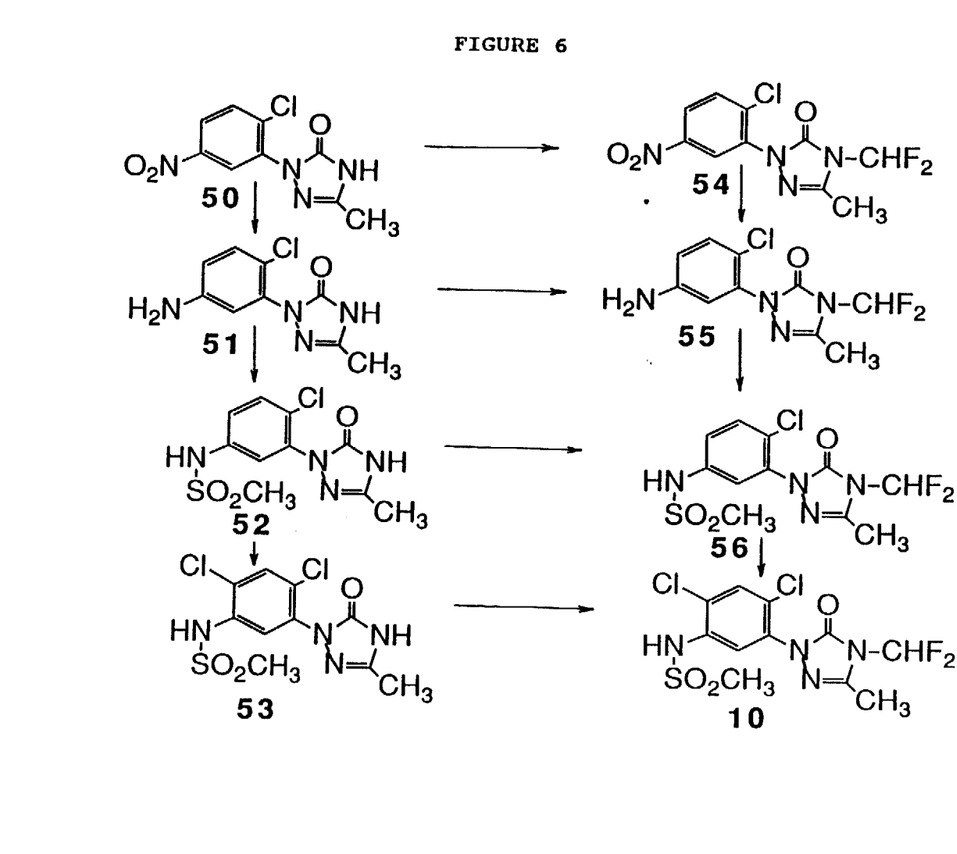
FIG. 6 shows reaction sequences starting with an intermediate, 4,5-dihydro-3-methyl-1-(2-chloro-5-nitrophenyl)-1,2,4-triazol-5(1H)-one, which is a known prior art compound.
Figure 7:
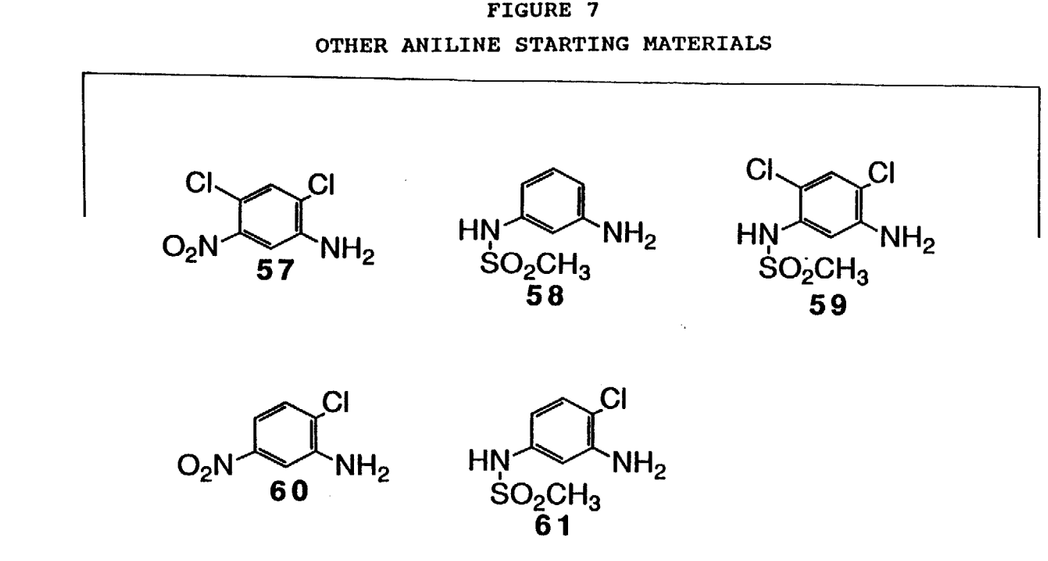
FIG. 7 shows various other substituted anilines which may be employed as starting materials.

A 0.5 g (0.00225 mol) sample of 3-methyl-1-(3-nitrophenyl)-1,2,4-triazolidin-5-one (compound 41, FIG. 5) was dissolved in 5 ml of glacial hypochlorite (Clorox ® household bleach; Clorox is a registered trademark) was added over a period of about 5 minutes. During this addition a precipitate formed in the initially clear reaction mixture. The mixture was then diluted with about 10 ml of water and filtered. The resulting solid was then dried, giving 0.41 g of material, which was identified by nmr as 4,5-dihydro-3-methyl-1-(3-nitrophenyl)-1,2,4-triazol-5(1H)-one (compound 42, FIG. 5).

In this experiment the filtrate, which may have contained an additional amount of product (see Example 2 below), was discarded.

EXAMPLE 2

To a stirred, warm (40° C.) solution of 66.2 g (0.37 mole) of acetaldehyde 3-nitrophenylhydrazone (compound 40, FIG. 5) in one liter of acetic acid was added a solution of 30.0 g (0.37 mole) of potassium cyanate in 75 ml of water. The reaction mixture was cooled to 20° C. and stirred for 30 minutes. An aqueous 5% sodium hypochlorite solution (600 ml) was added to the mixture during a 30 minute period while maintaining a temperature of 20° C. A precipitate formed during the addition. After this addition was complete, the mixture was diluted with one liter of water and was filtered; the filtrate was saved for further use. The filter cake was triturated with a solution of ethyl acetate:n-heptane (1:1) and was filtered. The solid thus collected was dried under reduced pressure to yield 52.4 g of 4,5-dihydro-3-methyl-1-(3-nitrophenyl)-1,2,4-triazol-5(1H)-one.

The filtrate, which had been saved above, was saturated with sodium chloride and then was extracted with two 750 ml portions of ethyl acetate. These extracts were combined with the filtrate from the trituration above, and the solvent was removed by evaporation under reduced pressure leaving a residue. This residue was stirred in approximately 500 ml of acetic acid, and approximately 200 ml of an aqueous 5% sodium hypochlorite solution was added. This mixture was stirred at room temperature for one hour during which time a precipitate formed. This precipitate was collected by filtration and was dried to yield an additional 13.7 g of product.

The nmr spectra of both portions were identical and were consistent with the proposed structure.

EXAMPLE 3

Figure 2:
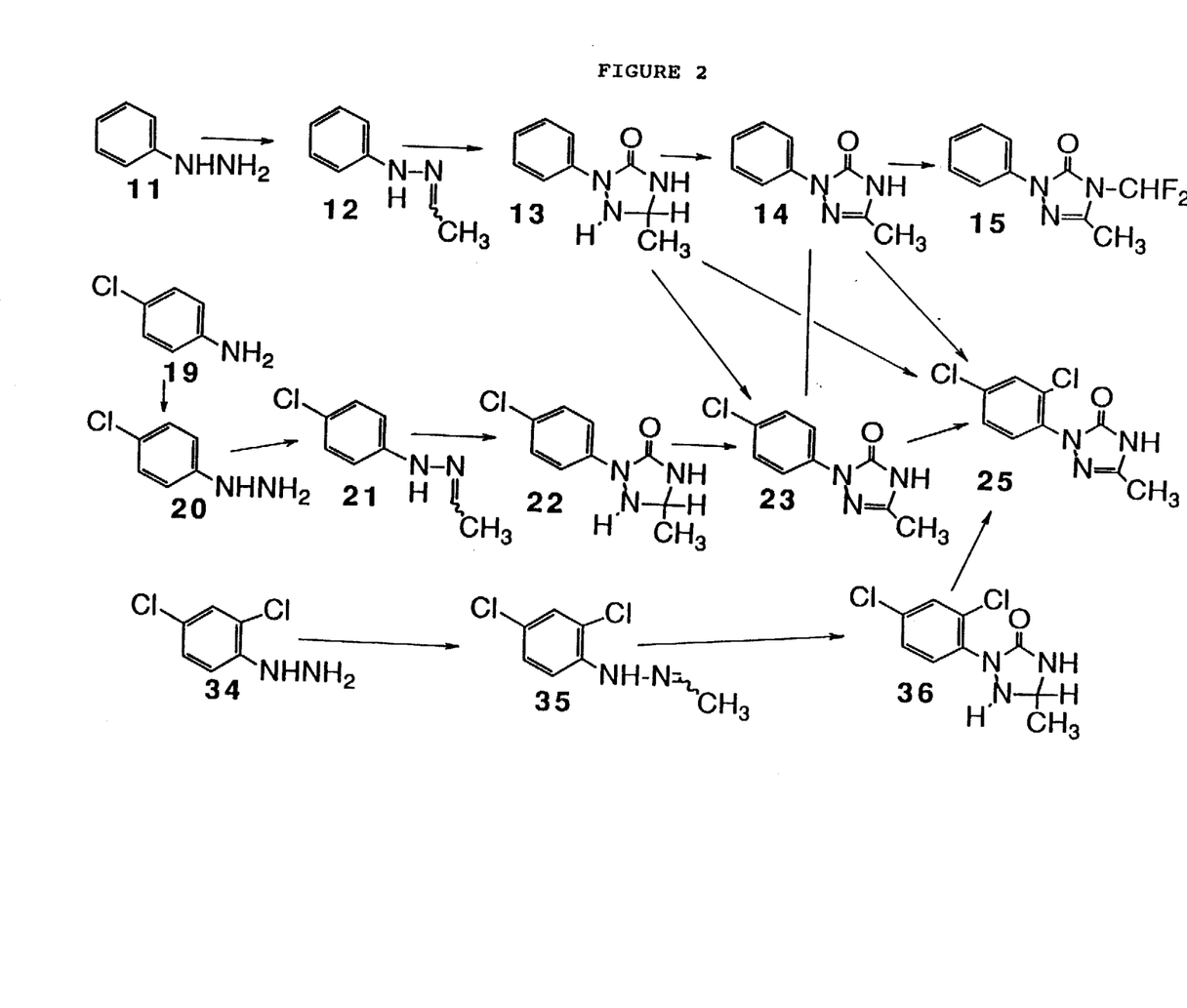
FIG. 2 shows reaction sequences starting with phenylhydrazine, 4-chloroaniline and 2,4-dichlorophenylhydrazine, producing intermediates.
Figure 3:
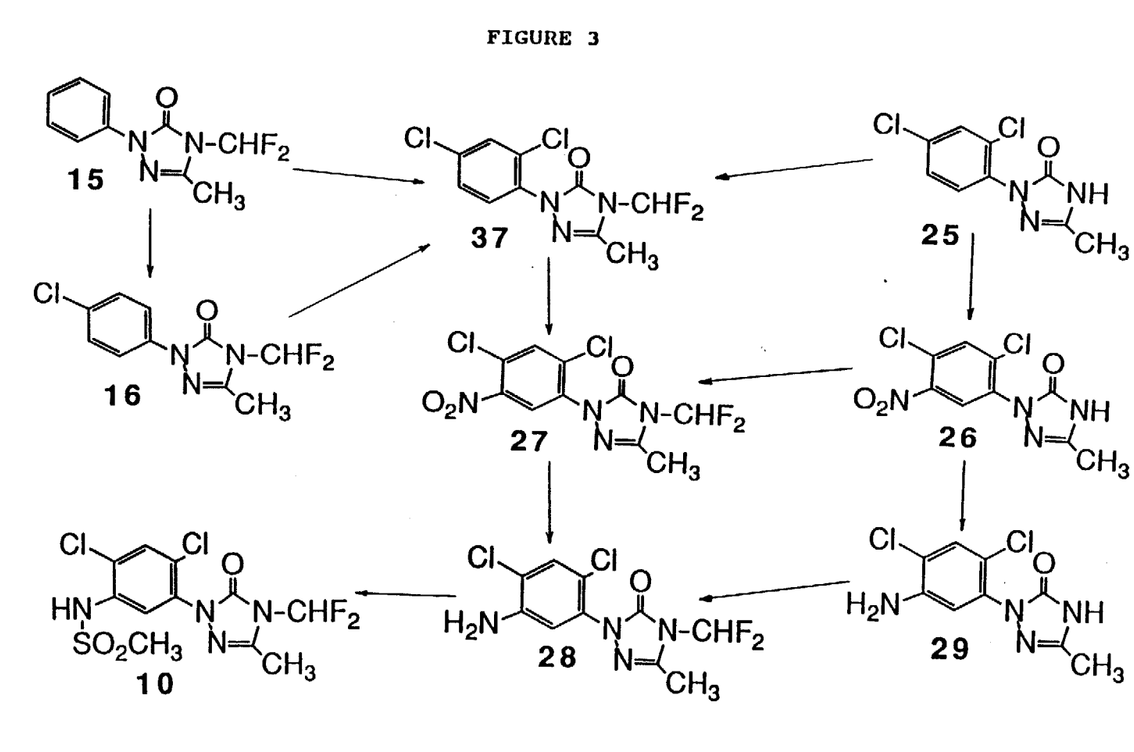
FIG. 3 shows continuations of the sequences of FIG. 2.
Figure 4:
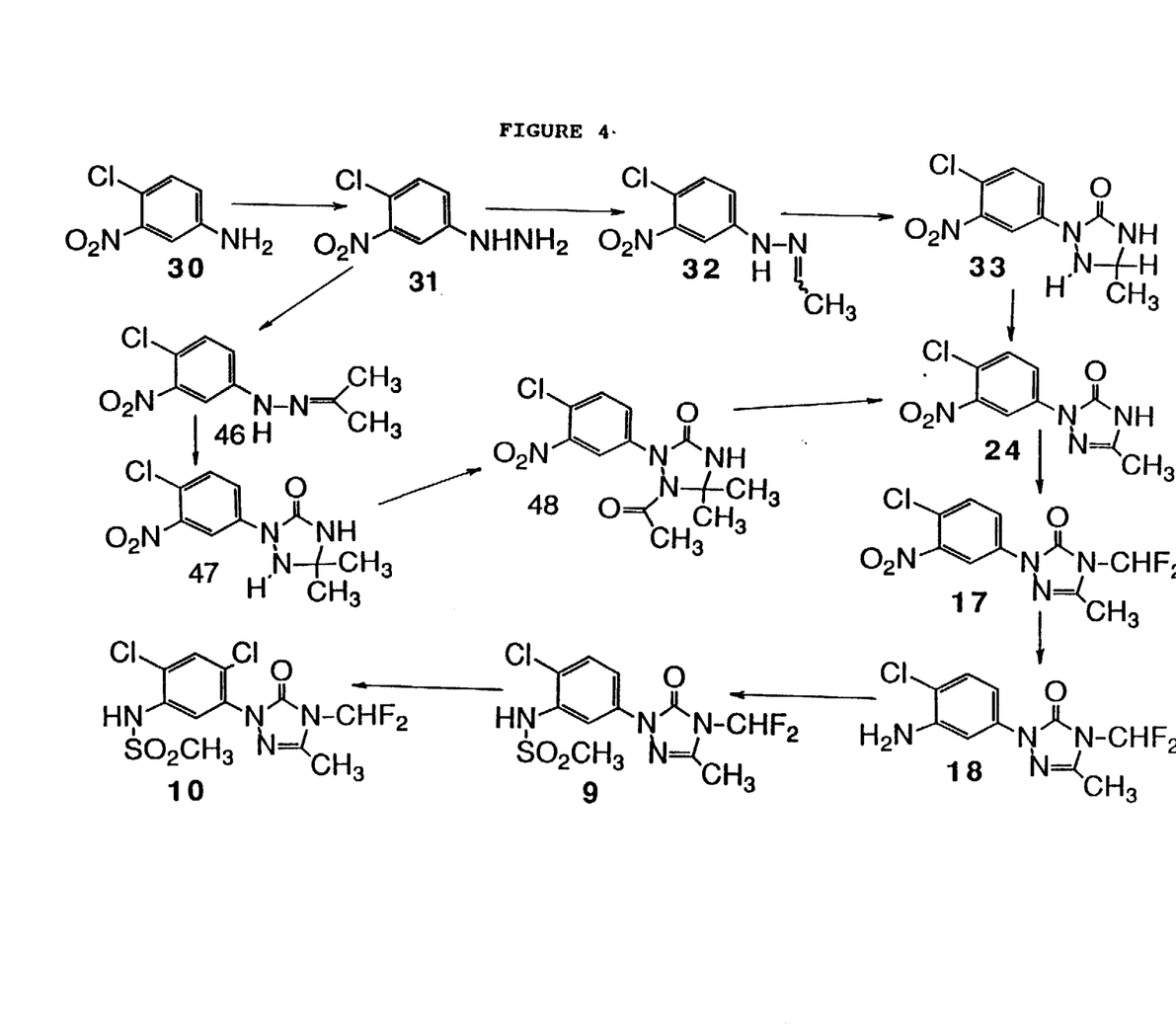
FIG. 4 shows reaction sequences starting with 4-chloro-3-nitroaniline.

A 20.0 g (0.170 mol) sample of 3-methyl-1-phenyl-1,2,4-triazolidin-5-one (compound 13, FIG. 2) was dissolved in 350 ml of aqueous 5% sodium hypochlorite (Clorox bleach) and stirred at room temperature. After 10 minutes the mixture became cloudy, the temperature had risen to 35° C., bubbling took place and an oily solid formed on the surface. Sodium hydroxide (7.0 g, 0.17 mol) was incorporated into the mixture, which was then extracted with diethyl ether to remove impurities, after which the aqueous phase was neutralized with HCl. A precipitate formed; it was collected by filtration and recrystallized from ethyl acetate/heptane 40/15 to give 13.50 g of a solid melting at 160°–165° C., 4,5-dihydro-3-methyl-1-phenyl-1,2,4-triazol-5(1H)-one (compound 14, FIG. 2).

EXAMPLE 4

To a stirred solution of 21.3 g (0.197 mol) of phenyl hydrazine (compound 11, FIG. 2) in 75 ml of glacial acetic acid, cooled to about 9° C., there was added, dropwise over a period of 2 minutes, a solution of 9.36 g (0.213 mol) of acetaldehyde in 12 ml of glacial acetic acid; this caused a gradual exotherm, with the temperature rising to about 18° C. Analysis of a sample taken ten minutes after the addition indicated a 94.4% yield of the desired hydrazone. Then a solution and the reaction was allowed to proceed to substantial completion to form the phenyl triazolidinone (compound 13, FIG. 2). The reaction mixture was then cooled to 14° C., and an aqueous 12% sodium hypochlorite solution was added slowly, and in spaced stages, until TLC analysis indicated that substantially no unreacted phenyl triazolidinone remained. The first addition was 136 ml, starting at 14° C. and rising to below 25° C., and resulted in the formation of an orange yellow suspension; in the next stages 50 ml (at room temperature followed by heating to 40° C.) and then 40 ml (at 34°–40° C.) were added. The reaction mixture was then filtered, and the filter cake was washed with water and then dried, under reduced pressure, at about 80° C., yielding 25.3 g of a light yellow orange powder (m.p. 154°–156° C.) which GC assay indicated was 97.6% 4,5-dihydro-3-methyl-1-phenyl-1,2,4-triazol-5(1H)-one (compound 14, FIG. 2).

EXAMPLE 5

Step A: To a cold (−10° C.), stirred solution of 5.0 g (0.039 mole) of 4-chloroaniline in 20 ml of sulfuric acid was added dropwise a solution of 3.9 ml of nitric in 5 ml of sulfuric acid. The reaction mixture was stirred at −10° C. for 30 minutes and then was diluted with 25 ml of acetic acid, 50 g of ice, and 25 ml of water. A solution of 2.7 g (0.039 mole) of sodium nitrite in 10 ml of water was added slowly to the stirred mixture while maintaining a temperature of 0° C. After complete addition, a solution of 17.7 g (0.0785 mole) of tin (II) chloride dihydrate in 25 ml of hydrochloric acid was added dropwise. After complete addition, the resultant mixture was stirred at −5° C. for 30 minutes. A solution of 3.94 g (0.0894 mole) of acetaldehyde in 50 ml of water was added. The reaction mixture was warmed to room temperature and stirred for 30 minutes, forming a precipitate. This solid was collected by filtration and the filter cake was dissolved in ethyl acetate. This organic solution was dried over anhydrous magnesium sulfate and was filtered. The filtrate was evaporated under reduced pressure to yield 5.4 g of acetaldehyde 4-chloro-3-nitrophenylhydrazone.

Step B: To a stirred solution of 5.25 g (00246 mole) of acetaldehyde 4-chloro-3-nitrophenylhydrazone in 25 ml of acetic acid was added dropwise a solution of 2.0 g (0.0246 mole) of potassium cyanate in 5 ml of water. After complete addition, 50 ml of an aqueous 5% sodium hypochlorite solution was added dropwise, forming a precipitate. After about ½ hour, the solid was collected by filtration and dried to yield 5.4 g of 1-(4-chloro-3-nitrophenyl)-4,5-dihydro-3-methyl-1,2,4-triazol-5(1H)-one.

The nmr spectrum was consistent with the proposed structure.

EXAMPLE 6

A 2.25 g (0.010 mol) sample of 3-methyl-1-(3-nitrophenyl)-1,2,4-triazolidin-5-one (compound 41, FIG. 5) was dissolved in 50 ml of glacial acetic acid, and chlorine gas was sparged in slowly causing the temperature (initially 22° C.) to rise to 37° C. followed by rapid precipitation of a yellow solid, at which time the introduction of the gas was discontinued and the mixture was stirred for 20 minutes, then filtered. The solid product was washed with acetic acid and dried under reduced pressure giving 1.65 g of a white powder. The filtrate was concentrated by evaporation at reduced pressure, to half their volume, forming additional precipitate which was recovered by filtration and dried, giving an additional 0.15 g of product. Nmr analysis confirmed that the product was 4,5-dihydro-3-methyl-1-(3-nitrophenyl)-1,2,4-triazol-5(1H)-one (compound 42, FIG. 5).

EXAMPLE 7

Chlorine gas was bubbled into a solution of 17.7 g (0.1 mol) of 3-methyl-1-phenyl-1,2,4-triazolidin-5-one (compound 13, FIG. 2) in about 10 times its weight of glacial acetic acid at room temperature for 5 minutes. The temperature rose to 35° C., and the brown solution became lighter in color. Nmr analysis showed that the product was 4,5-dihydro-3-methyl-1-phenyl-1,2,4-triazol-5(1H)-one (compound 14, FIG. 2). Next 1.0 g of iron powder was slowly added to the mixture, and it was heated to 95° C. and chlorine gas was bubbled into it for 10 minutes, after which it was maintained at the elevated temperature for one hour with stirring. The mixture was then dumped into ice, extracted with ethyl acetate, dried over magnesium sulfate and passed through a column of silica gel, (which was then eluted with 200 ml of ethyl acetate to give a solution from which the solvent was then evaporated under reduced pressure), giving 12.0 g of a solid (m.p. 174°–176° C.), 4,5-dihydro-3-methyl-1-(4-chlorophenyl)-1,2,4-triazol-5(1H)-one (compound 23, FIG. 2).

EXAMPLE 8

Acetaldehyde 4-chloro-3-methylsulfonylaminophenylhydrazone (compound 6, FIG. 1) (in the amount of 2.0 g, 7.64 mmols) was dissolved in 40 ml of glacial acetic acid, and 0.50 g (7.64 mmols) of sodium cyanate was added all at once with stirring. After 5 minutes, about 14.8 ml of aqueous 5% sodium hypochlorite (Clorox bleach) (about 9.9 mmols) was added with stirring. After another 5 minutes a precipitate formed. To this mixture was added 6 ml of 6N HCl, and the whole was concentrated under reduced pressure to give a solid. The solid was then washed with 150 ml of water and dried in vacuo, yielding 1.95 g of a material which, by nmr analysis, contained 94% of 4,5-dihydro-3-methyl-1-(4-chloro-3-methylsulfonylaminophenyl-1,2,4-triazol-5(1H)-one (compound 8, FIG. 1) and 6% of 3-methyl-1-(4-chloro-3-methylsulfonylaminophenyl)-1,2,4-triazolidin-5-one (compound 7, FIG. 1).

To prepare the starting material, acetaldehyde 4-chloro-3-methylsulfonylaminophenylhydrazone, a mixture of 20.0 5 (116 mmoles) of 2-chloro-5-nitroaniline (compound 4, FIG. 1), 24.6 g (243 mmoles) of triethylamine and 100 ml of methylene chloride was cooled in an ice bath, and a solution of 27.8 g (243 mmols) of methylsulfonyl chloride in 20 ml of methylene chloride was added dropwise. When the addition was about half complete the ice bath was removed. After completion of the addition, the mixture was allowed to stand for an hour and then filtered to remove undesired salts. The filtrate was evaporated under reduced pressure to give a yellow solid which was washed with 100 ml of water; the filter cake was then mixed with 100 ml of ethanol and then filtered rapidly, and the resulting off-white solid was dried in vacuo to give 32.7 g of 2-chloro-5-nitro-1-bis(methylsulfonyl)amino-benzene. The latter was then mixed with 50 ml of ethanol; 8 g of NaOH in 20 ml of water was added slowly with stirring, after which the mixture was diluted with 300 ml of water followed by the addition of 45 ml of 6N HCl, yielding a precipitate which was collected by filtration and dried in vacuo to give 24.3 g of 2-chloro-5-nitro-1-methylsulfonylaminobenzene (compound 4, FIG. 1). The latter material was reduced with iron powder to form 17.7 g of 4-chloro-3-methylsulfonylaminoiline.

Figure 1:
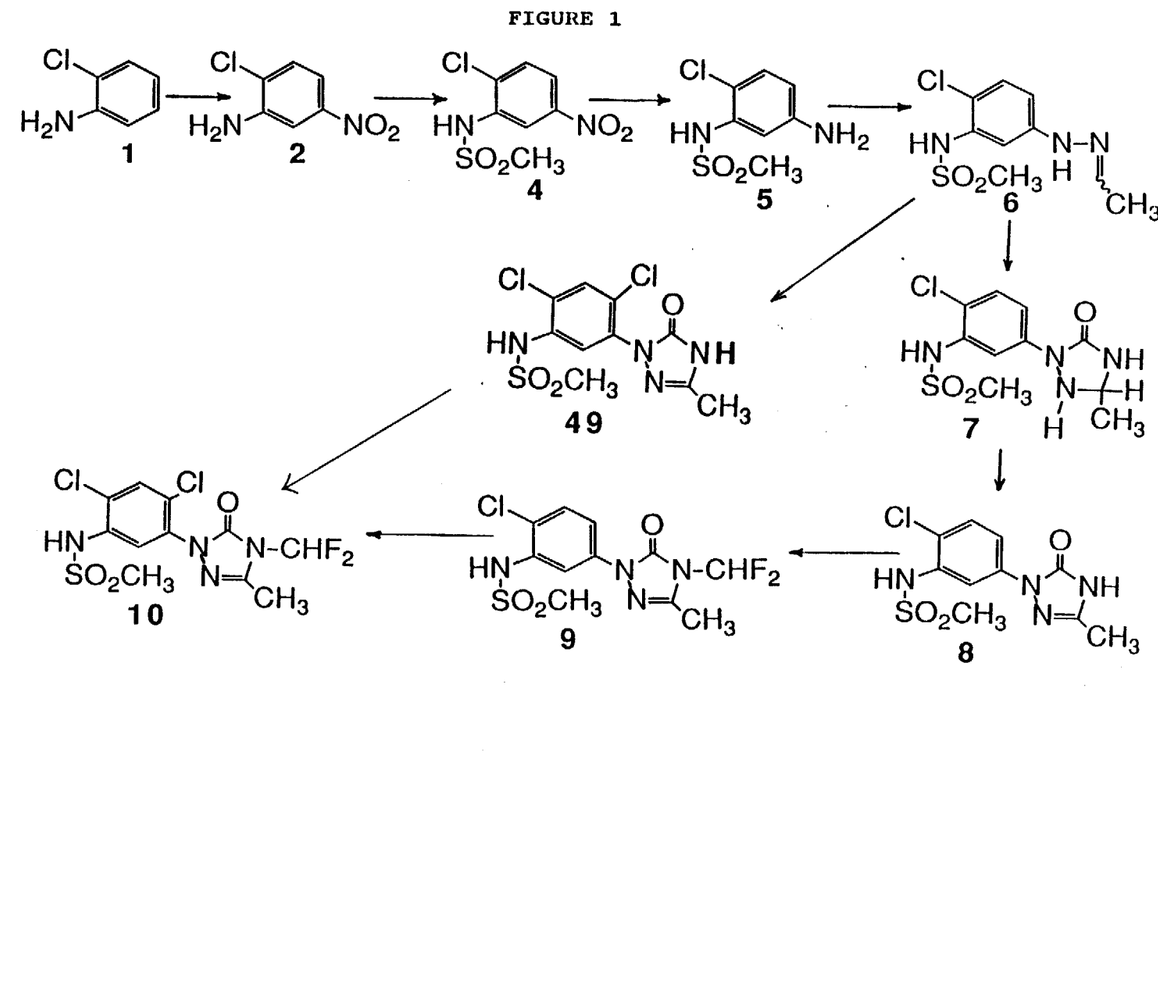
FIG. 1 shows a reaction sequence starting with 2-chloroaniline.

More particularly, the reduction of compound 4 was effected by mixing the nitro compound with 90 ml of acetic acid, 90 ml of methanol and 15 ml of water and heating the mixture to reflux, then adding 16.2 g of iron powder over a 15 minute period while maintaining reflux, then refluxing for an additional hour, filtering, concentrating the filtrate under reduced pressure, partitioning the residue between saturated aqueous solution of sodium bicarbonate (200 ml)/tetrahydrofuran (150 ml)/diethyl ether (300 ml) and then concentrating the resulting ethereal solution under reduced pressure to give an off-white solid.

The 4-chloro-3-methylsulfonylaminoaniline was then converted to the corresponding acetaldehyde hydrazone (compound 6, FIG. 1) by diazotization (with NaNO$_2$/HCl), reduction of the diazo salt (as with stannous chloride) to form the hydrazine and then reaction of the hydrazine with acetaldehyde, all in one reaction vessel. More particularly, 10.0 g of the 4-chloro-3-methylsulfonylaminoaniline and 60 ml of aqueous concentrated HCl were mixed and cooled to about 0° C. A solution of 3.44 g of sodium nitrite in 16 ml of water was added, in portions, below the surface of the reaction mixture, maintained at 0 to −5° C. Then, after the mixture was allowed to warm to +5° C. and then cooled to −10° C., a solution of 22.6 g of SnCl$_2$ in 26 ml of aqueous concentrated HCl was added dropwise, and the mixture was allowed to warm slowly to room temperature. It was then diluted with 50 ml of water at 5° C. and then 100 ml of water at 20° C., after which 4.4 g of acetaldehyde was added. The mixture was then extracted with tetrahydrofuran (50 ml)/diethyl ether (300 ml). The ethereal solution was washed with water (100 ml) and a saturated aqueous solution of sodium bicarbonate (about 100 ml) and concentrated under reduced pressure to give 8.4 g of the hydrazone.

EXAMPLE 9

In this Example the procedure was similar to that of Example 8, but the amount of NaOCl solution was increased to 18.2 ml (about 12.2 mmols) and the hypochlorite-containing reaction mixture was stirred for about 1.5 hours, after which the mixture was concentrated to give an oily solid which was purified, as described below, to give 1.80 g of a dry solid which, by nmr analysis was shown to contain 4-5% of 1-(4-chloro-3-methylsulfonylaminophenyl)-4,5-dihydro-3-methyl-1,2,4-triazol-5(1H)-one (compound 8, FIG. 1) and 55% of 1-(2,4-dichloro-5-methylsulfonylaminophenyl)-4,5-dihydro-3-methyl-1,2,4-triazol-5(1H)-one (compound 49, FIG. 1).

The purification method involved dissolving the oily solid in a mixture of 75 ml of tetrahydrofuran and 150 ml of diethyl ether, washing the resulting solution with 100 ml of water and evaporating the solvent from the ethereal solution.

EXAMPLE 10

To a stirred mixture of 5.0 g (0.023 mole) of acetaldehyde 4-chloro-3-nitrophenylhydrazone in 50 ml of acetic acid was added dropwise a solution of 1.95 g (0.024 mole) of potassium cyanate in 5 ml of water. The resultant mixture was stirred at 15° C. for 1.5 hour. An additional 0.25 g (0.0031 mole) of potassium cyanate in 2 ml of water was added dropwise. This mixture was stirred for one hour. While maintaining a temperature of 15° C., 42.9 ml of an aqueous, 5% sodium hypochlorite solution was added dropwise. The resultant mixture was stirred at 15° C. for one hour. The solvents were removed by distillation under reduced pressure leaving a solid residue. This solid was stirred in 100 ml of toluene. The solvent was removed by evaporation under reduced pressure leaving a solid residue. The solid residue was dissolved in 150 ml of ethyl acetate. This solution was washed in succession with an aqueous, saturated sodium bicarbonate solution, water, and an aqueous, saturated sodium chloride solution. The washed organic phase was dried over anhydrous magnesium sulfate and was filtered. The filtrate was evaporated under reduced pressure to yield 5.77 g of 4,5-dihydro-3-methyl-1-(4-chloro-3-nitrophenyl)-1,2,4-triazol-5(1H)-one as a solid.

The nmr spectrum was consistent with the proposed structure.

We claim:

1. Process for the production of an aryl triazolinone of the formula:

Formula I in which
R is halogen, alkyl, haloalkyl, cyanoalkyl, arylalkyl, alkoxyalkyl, alkylthio, alkylsulfinyl, alkylsulfonyl, alkylthioalkyl, alkylsulfinylalkyl, alkylsulfonylalkyl or phenyl,
each X is independently, H, halogen, lower alkyl, lower alkoxy, —NO$_2$, —OH, —NHSO$_2$R', —N(SO$_2$R')$_2$ or —N(R')SO$_2$R' where R' is lower alkyl, and n is a number from 1 to 3, by treating an aryl triazolidinone of the formula:

Formula II with a halogen of the group consisting of chlorine, bromine and iodine, or a hypohalous acid of said halogen or a salt of said acid.

2. Process as in claim 1 in which said halogen is chlorine.

3. Process as in claim 1 in which said compound of Formula II is treated in a solution or suspension thereof.

4. Process as in claim 3 in which said compound of Formula II is treated in a suspension thereof in a liquid medium in which said compound of Formula II is partly soluble.

5. Process as in claim 3 in which said compound of Formula II is treated in a solution thereof.

6. Process as in claim 2 in which said compound of Formula II is treated with chlorine gas.

7. Process as in claim 2 in which said compound of Formula II is treated with a hypochlorite.

8. Process as in claim 1 in which $x_n$ in Formula II is 3-$NO_2$.

9. Process as in claim 1 in which $x_n$ in Formula II is 2,4-dichloro.

10. Process as in claim 1 in which $x_n$ in Formula II is hydrogen.

11. Process as in claim 1 in which $x_n$ in Formula II is 4-chloro-3-nitro.

12. Process as in claim 1 in which $x_n$ in Formula II is 4-chloro-3-methylsulfonylamino.

13. Process as in claim 1 in which $x_n$ in Formula II is 4-chloro.

* * * * *

UNITED STATES PATENT AND TRADEMARK OFFICE
CERTIFICATE OF CORRECTION

PATENT NO. : 4,980,480
DATED : December 25, 1990
INVENTOR(S) : George Theodoridis and John W. Lyga It is certified that error appears in the above-indentified patent and that said Letters Patent is hereby corrected as shown below:

Column 5, line 28 of Example 4, after "solution" insert —of 16.8 g of KOCN in 34 ml of water was added dropwise,—

Signed and Sealed this

Sixteenth Day of September, 1997

Attest:

BRUCE LEHMAN

Attesting Officer

Commissioner of Patents and Trademarks